United States Patent [19]

Berthold et al.

[11] 4,435,509

[45] Mar. 6, 1984

[54] ASSAYS, INCLUDING IMMUNOASSAYS WITH FITC LABEL ACTIVATED BY SODIUM HYPOCHLORITE

[75] Inventors: Fritz Berthold, Pforzheim; Helmut Kubisiak, Wildbad, both of Fed. Rep. of Germany

[73] Assignee: Laboratorium Prof. Dr. Rudolf Berthold, Wildbad, Fed. Rep. of Germany

[21] Appl. No.: 294,563

[22] Filed: Aug. 20, 1981

[30] Foreign Application Priority Data

Aug. 22, 1980 [DE] Fed. Rep. of Germany ....... 8027422

[51] Int. Cl.$^3$ ..................... G01N 33/52; G01N 33/54; G01N 33/58; G01N 33/68
[52] U.S. Cl. .................................... 436/518; 436/86; 436/172; 436/536; 436/546; 436/800
[58] Field of Search ................... 424/8, 12; 23/230 B; 436/86, 172, 518, 536, 546, 800

[56] References Cited

U.S. PATENT DOCUMENTS 4,104,029 8/1978 Maier ................................ 23/230 B
4,238,195 12/1980 Boguslaski ...................... 23/230 B

OTHER PUBLICATIONS

Simpson et al, "A stable chemiluminesent-labelled antibody for immunological assay", Nature, vol. 279, Jun. 1979, pp. 646 and 647.
Erkki Soini et al, "Fluoroimmunoassay: Present Status and Key Problems", Clinical Chemistry, vol. 25, No. 3, 1979, pp. 353 to 361.
Robert Nilsson et al, "Role of Singlet Oxygen in Some Chemiluminescence and Enzyme Oxidation Reactions", The Journal of Physical Chemistry, vol. 78, No. 17, Aug. 15th, 1974, pp. 1681 to 1683.
J. L. Riggs et al, "Isothiocyanate Compounds as Fluorescent Labeling Agents for Immune Serum", Amer. I. Pathol., vol. 34, No. 6, pp. 1081 to 1092.
John D. Marshall et al, "Superiority of Fluorescein Isothiocyanate (Riggs) for Fluoroscent-Antibody . . . ", Proc. Soc. Experimental Biol. Med., vol. 98, 1958, pp. 898 to 900.
Fiorenzo Paronetto, "The Fluorescent Antibody . . . ", Proc. Soc. Experimental Biol. Med., vol. 113, 1963, pp. 394 to 397.
Pressman et al, The Structural Basis of Antibody Specificity, W. A. Benjamin, Inc., 1968, pp. 8 to 15, New York, 1968.

*Primary Examiner*—Sidney Marantz
*Attorney, Agent, or Firm*—Spencer & Frank

[57] ABSTRACT

Process for carrying out an analytical determination of the presence of a substance by means of chemiluminescence, comprising employing fluorescein isothiocyanate (FITC) as a labelling agent, triggering a chemiluminescence reaction by adding an aqueous solution of sodium hypochlorite, and measuring the emission of light.

14 Claims, 3 Drawing Figures

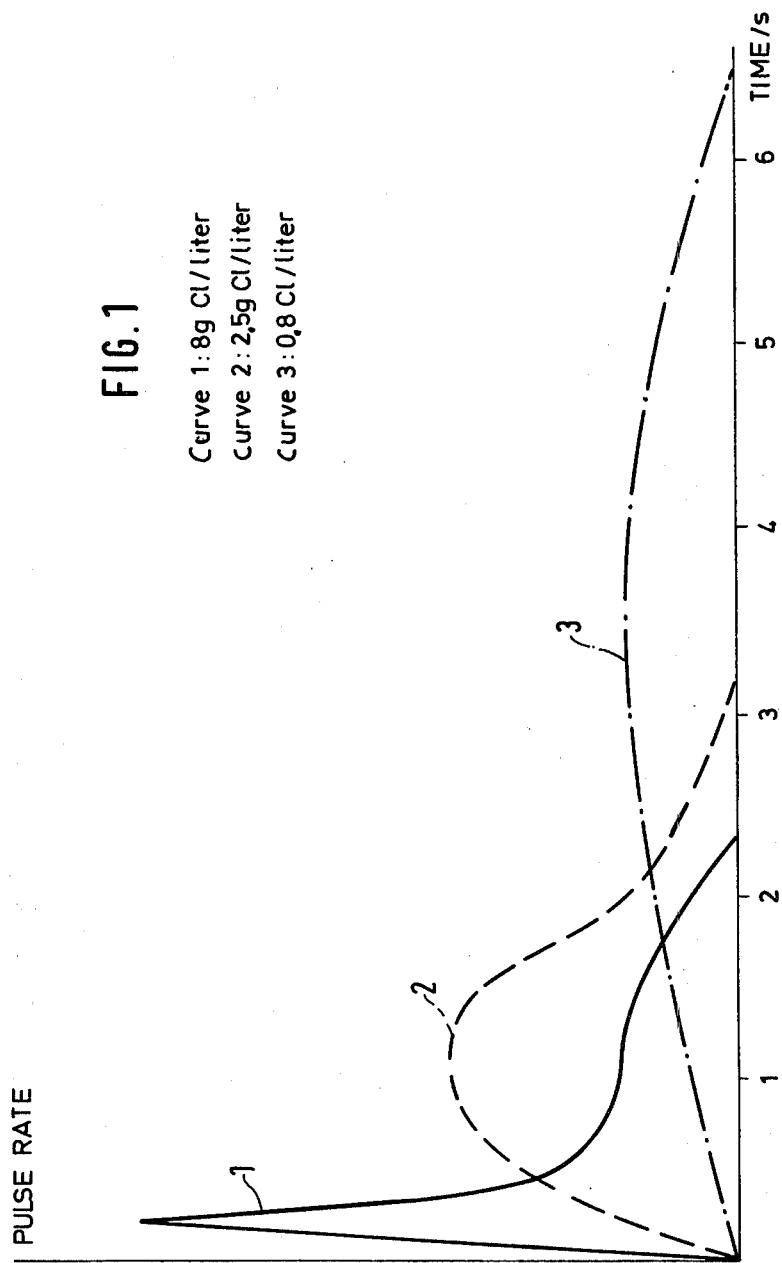

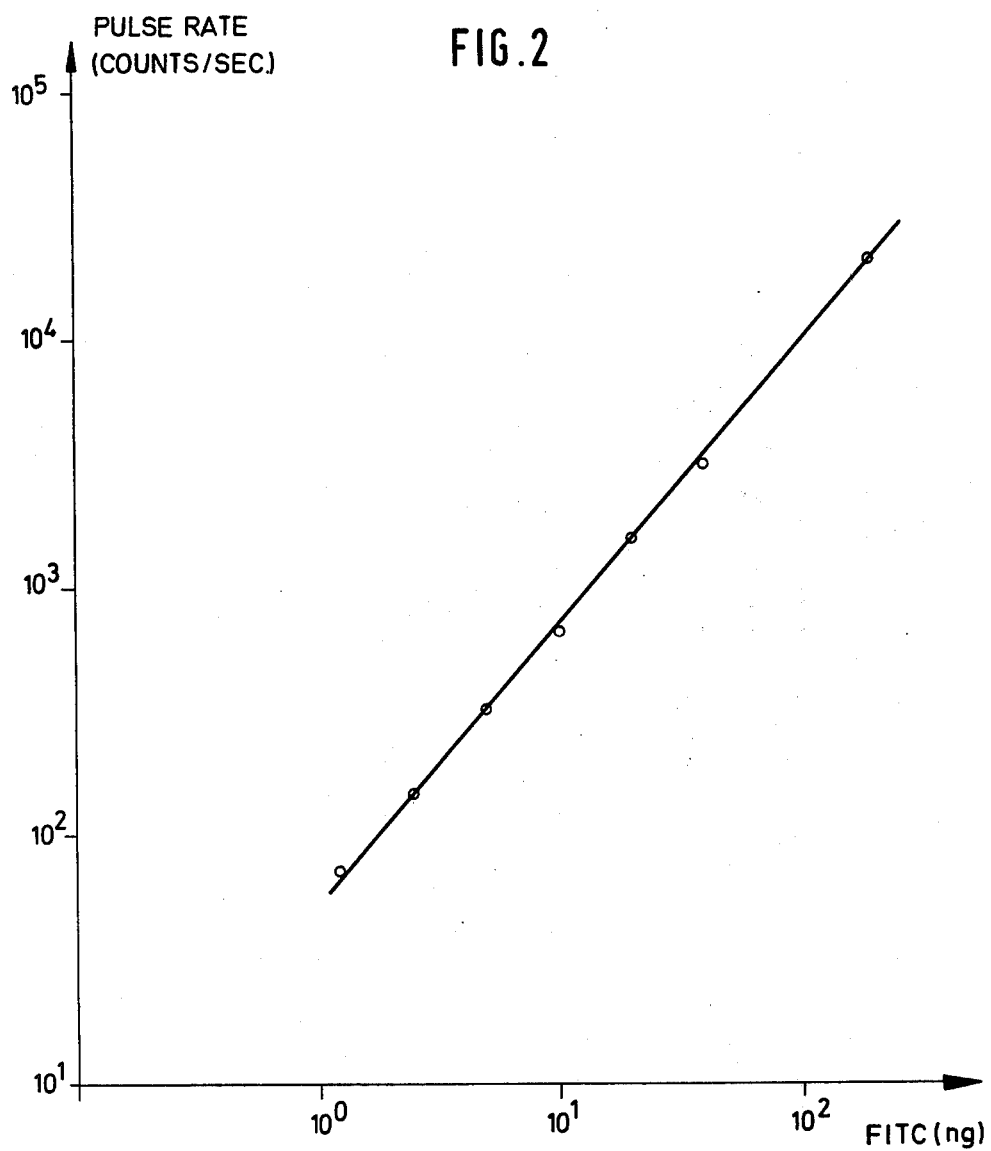

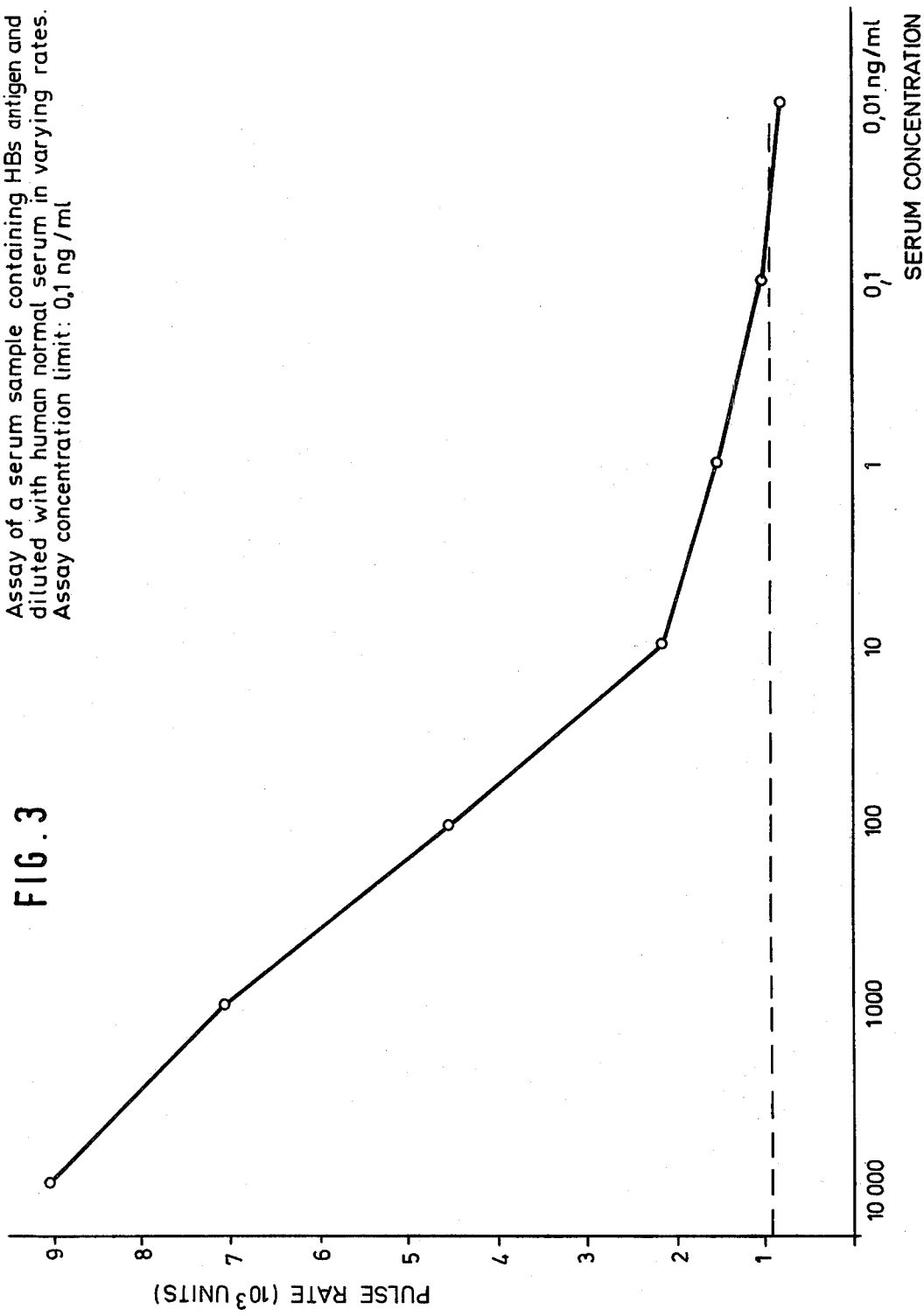

ASSAYS, INCLUDING IMMUNOASSAYS WITH FITC LABEL ACTIVATED BY SODIUM HYPOCHLORITE

BACKGROUND OF THE INVENTION

The present invention relates to the use of chemiluminescence in analytical determinations, for example, for immunoassay.

Chemiluminescence is a physical phenomenon which is based on a chemical reaction and is therefore fundamentally different from fluorescence. In fluorescence, a molecule is excited by visible light or UV light, but remains unchanged and merely reradiates (emits) the absorbed light. The emission is either at the same wavelength as the absorbed light or a longer wavelength.

In contrast, the mechanism of chemiluminescence is based on the formation of high-energy, unstable intermediate products which decompose, with emission of light, to give an end product.

Analytical processes which utilize fluorescence are known per se, but background fluorescence has been found to affect seriously the results obtained, and has made it necessary to employ some expedient to eliminate this interfering fluorescence from the measurement.

Thus, according to German Offenlegungsschrift No. 2,628,158, the effect of background fluorescence is avoided by using as the labelling material only those fluorescent substances which, with appropriate excitation and at room temperature, have a narrow fluorescence spectrum coupled with a long decomposition time, and also by ensuring, by an appropriate scanning mechanism, that the measurement takes place only at a point in time when the interfering or competing fluorescence has already decayed, i.e. after about 100 nanoseconds.

The method disclosed in German Offenlegungsschrift No. 2,628,158 has, however, the disadvantages that the actual measurement, in each case, can only take place after the decay phase, and that relatively expensive equipment is required to couple the radiation pulse to the detection device so that the measurement is made not too early or too late.

A summary of the difficulties which occur in fluorescence immunoassay processes may be found in "Clinical Chemistry" (1979), pages 353-361.

Proposals to utilize chemiluminescence for quantitative analytical processes have been based on the property of, in particular, the organic compound known by the name luminol, i.e. that luminol reacts with oxygen in alkaline solution and thereby forms an unstable intermediate product which then decomposes, with emission of light. See, for example, U.S. Pat. No. 4,104,029, to Charles L. Maier, Jr., issued Aug. 1, 1978.

However, this method has not found acceptance in analytical practice, especially in immunoassay, probably mainly because when luminol is subjected to the chemical modification necessary to enable it to be coupled to proteins of the antigen and antibody type, its molecular structure is altered such that the reaction required for chemiluminescence is impaired. This view is also supported by the observations made by Simpson and co-workers (see, for example "Nature", Volume 279 (1979), pages 646/647) that the radiation intensity of diazotized luminol is only barely 1% of that of unmodified luminol.

A system in which fluorescein can be excited to luminescence by chemical processes is also described, in "Journal of Physical Chemistry", 78 (1974), pages 1681–1683.

In this reference, a system consisting of $H_2O_2$ and NaOCl is used as a reactant for the chemiluminescence reaction. However, it was reported that the concentration of the fluorescein required for detection is extremely high. The smallest amount detected was $2 \times 10^{-4}$ mol, so that, compared with the requirements of immunoassay, the sensitivity is at least six orders of magnitude too low. It was also reported that the life of the luminescence in the system mentioned is only $2\mu$ s, that is to say, the emission of photons takes place instantaneously. These very rapid kinetics are completely unsuitable for sensitive measurement. Photon counters are used for detecting the photons because they are the most sensitive measuring devices, but because of their typical dead time of 20 ns, only limited maximum pulse rates can be processed. Quantitative and sensitive measurement of luminescence phenomena which takes place instantaneously is thus impossible.

In order to enable the chemiluminescence method to be applied to immunoassay, it would be desirable to achieve the following:

1. The sensitivity should be increased so that as little as $10^{-10}$ mol of the labelling agent can be detected.
2. The reaction kinetics should be changed so that the emission of light does not take place instantaneously but, for example, over a period of several seconds.

It would furthermore be desirable:

3. to initiate the luminescence not by the addition of two reagents ($H_2O_2$+NaOCl), but only by a single reagent. This would on the one hand simplify the measuring equipment (only one dispenser would be required, instead of two). Also, however, when two reagents are mixed, even in the absence of the chemiluminescent substance to be detected, considerable background luminescence is produced. This background is pronounced in the case of the system $H_2O_2$/NaOCl, and furthermore is not constant, so that there are again the disadvantages known in the case of fluorescence.

SUMMARY OF THE INVENTION

A primary object of the present invention is to make the phenomenon of chemiluminescence applicable to analysis methods, and in particular immunoassay, in a manner which can be utilized in practice.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve the foregoing objects and in accordance with its purpose, the present invention provides a process for carrying out analytical determinations by means of chemiluminescence, comprising employing fluorescein isothiocyanate (FITC) as a labelling agent, triggering a chemiluminescence reaction by adding an aqueous solution of sodium hypochlorite, and measuring the emission of light.

In a preferred embodiment, the determination is carried out in an aqueous medium without the addition of other oxidising agents and/or reducing agents for the chemiluminescence reaction.

The present invention employs a surprisingly effective novel system of labelling material and oxidising agents which permits a high yield of photons and yet also, when the labelling material is coupled with, for example, proteins, aminoacids or polysaccharides, it does not suffer a troublesome decrease in reactivity towards the oxidising agent which induces the formation of the unstable intermediate products. This system is also sufficiently stable and sensitive for it to be possible for even very low concentration of the labelling agent to be measured with a high accuracy.

DESCRIPTION OF THE DRAWINGS

The accompanying drawings, in which like numbers indicate like parts, illustrate examples of presently preferred embodiment of the invention and, together with the description, serve to explain the principles of the invention.

Of the drawings:

FIG. 1 is a graph which illustrates the kinetics of a luminescence reaction employing FITC as a chemiluminescence material.

FIG. 2 is a graph which illustrates the effect of FITC concentration on pulse rate.

FIG. 3 is a graph which illustrates test results for an immunoassay for $HB_s$ antigens in human serum employing FITC as a labelling materal in accordance with the teachings of the present invention.

DETAILED DESCRIPTION OF THE INVENTION

In the practice of the present invention, the substance which is to be determined can be any one of a wide variety of materials such as proteins, amino acids, and polysaccharides. As exemplary of the substances which can be determined in accordance with the present invention, reference is made to the list of substances which appears at column 5, lines 10 to 55 of U.S. Pat. No. 4,104,029 which is hereby incorporated by reference.

Generally, the substance which is to be determined, also referred to herein as a target substance, is one which can be reacted with or coupled to a receptor or binding agent which has a good specificity and affinity for the substance to be determined. The FITC, as described in detail hereafter, can be coupled initially either to the substance to be determined or to the binding agent. After the substance to be determined, the FITC, and the binding agent have been contacted with each other, the resulting coupled product is subjected to further chemical reaction by adding aqueous NaOCl solution to induce chemiluminescence which is then measured.

Fluorescein isothiocyanate is a commercially available product and can be obtained, for example, from Messrs. EGA-Chemie, 7924 Steinheim, Federal Republic of Germany.

Generally, aqueous NaOCl solutions containing, for example, 2 to 100 g Cl/liter are used for the process according to the present invention. Commercially available NaOCl solutions contain about 150 to 155 g Cl per liter, and these commercial solutions can be diluted to bring them to the concentration used in the process of the present invention.

For determinations with FITC which is not bound to protein, sodium hypochlorite solutions containing, for example, 2.5 g Cl per liter are suitable. Depending on the chlorine content of the starting solution to be diluted, the hypochlorite solutions used for the chemiluminescence reaction may contain 0.01 to 3% and advisably 0.15 to 0.6% (weight/volume) of NaOCl.

For protein bound FITC, the chlorine content of the hypochlorite solution must be higher by the factor 10 so that it is advisable to employ solutions which contain about 25 g Cl per liter. In immunoassay, a protein bound FITC is always used.

The chemiluminescence induced by the oxidation reaction is recorded quantitatively by a suitable instrument for measuring photons, without a special radiation pulse being required, as is the case, for example, with fluorescence analysis.

The process according to the invention is suitable both for solid phase assay and for liquid phase assay.

The target substances in question which are to be labelled by the compound FITC, which can be excited to chemiluminescence, are first separated off from other substances in a known manner, for example by means of chromatography or by fixing to antibodies (in this context, see, for example, "Proc. Soc. Experimental Biology", Volume 113 (1963), pages 394–397).

For example, when the target substance to be determined is an antigen, the antibody specific for the target substance may be applied to a solid matrix substance, such as cellulose acetate, and the target substance to be investigated and to be determined analytically is brought into contact, in the form of a solution, with the antibody on the matrix and is thereby fixed on the substrate. The fixed target substance is then coupled to the labelling agent, i.e., the flourescein isothiocyanate (FITC), and the so-coupled labelling agent is subjected to further chemical reaction by adding aqueous NaOCl solution to induce chemiluminescence which is then measured.

The labelling agent may be coupled to the antibody or the antigen, depending on whether a direct, an indirect or an anti-complementary serological activity method is chosen, by known methods, such as have already successfully been used for the coupling of fluorescein, isothiocyanate (see for example, "Amer. J. Pathol.", Volume 34 (1958), page 1081 and "Proc. Soc. Experimental Biol. Med." 98 (1958), page 898 et seq.).

In the direct immunoassay method, for example for determining a certain antigen in blood serum, the serum in question is subjected to customary preparation techniques. Then the antigen is fixed onto a solid substrate, and subsequently combined with a specific antibody, coupled with the FITC. Finally, excess labelled antibody is separated off. The combined product is then subjected to further chemical reaction by adding aqueous NaOCl solution to induce chemiluminescence which is then measured.

According to the known "Sandwich" technique, which is described in "Proc. Soc. Ex. Biol." 113 (1963), page 394, a solid substrate with a deposit of antibody liquid is brought into contact with the sample to be investigated, the amount of antibody being greater than that required for bonding all the antigenic material in the sample. The substrate charged in this manner is then brought into contact with a solution containing the antibodies modified by the labelling agent, so that the antigens on the substrate become attached to these labelled antibodies. The substrate is then freed from excess labelled antibody and the solid substrate is subsequently treated with aqueous NaOCl solution in order to induce chemiluminescence which is then measured. This so-called "Sandwich" process is always particularly suitable if the antigen in question has more than one bonding point for an antibody, that is to say in general for antigens in the form of large molecules.

If the antigens in question are relatively small molecules which contain only a single antibody-specific bonding point per molecule, the indirect investigation process may be used. In this process, antigens which are identical to the material to be investigated are bonded to a solid substrate which forms a chemical bond with an antigen such that an antibody-specific bonding point or bond remains free. This process requires the formation of a chemical compound of the antigen in question and a protein, the bonding point on the antigen then remaining accessible to the animal immunological system, so that suitable antibodies can be produced, (in this context, compare "Structural Basis of Antibody Specificity", by Pressman and Grossberg, published by W. A. Benjamin, Inc. (1968), especially pages 9 and 10). A suitable solid substrate which can form a chemical combination with an antigen is, for example, a styrene polymer with side chains which contain functional groups of a type such that the side chains match a group on the antigen presently to be investigated. The solid substrate is then immersed in a solution containing an unknown amount of the antigen in question and the antibody specific to the antigen and modified by the labelling agent is subsequently added. The antigen contained in the solution and the antigen on the solid substrate compete for the labelled antibody, and the amount of the antibody which forms a combination with the solid substrated depends on the unknown amount of antigen in the solution. The amount of labelled antibody on the solid substrate is then determined by adding NaOCl solution and inducing chemiluminescence, and the amount of antigen in the solution can thus be determined.

The process according to the invention is of particular interest for virologic-serologic diagnosis, e.g. in the diagnosis of hepatitis A and B, in rubella, CMV (cytomegalovirus) and EBV (Epstein-Barr virus) serology. Additionally, in clinical chemistry there is great interest in sensitive and specific testing systems without radioactivity, for example for the diagnosis of diseases involving the thyroids (T3, T4), for the diagnosis of diabetes (insulin), etc.

The following examples are given by way of illustration to further explain the principles of the invention. These examples are merely illustrative and are not to be understood as limiting the scope and underlying principles of the invention in any way. All percentages referred to herein are by weight unless otherwise indicated.

Example I

Detailed measurements are made with unbound FITC (protein free) to determine the kinetics of the reaction, the results of which are shown in FIG. 1. Initially, it is found that the time sequence of the light emission, i.e. the kinetics, can clearly be set by way of the NaOCl dilution. Above a concentration of about 8 g Cl/liter (curve 1), there still is obtained the known flash-like or instantaneous light emission. Optimum kinetics are obtained in a range of about 2.5 g Cl/liter (curve 2), while with 0.8 g Cl/liter (curve 3), the kinetics became even slower, but sensitivity decreased considerably.

If instead of the unbound protein free FITC, protein bound FITC is used, different kinetics result as a function of the chlorine concentration. The chlorine concentration has to be increased by a factor of 10 to realize the same kinetics as for the unbound FITC.

The measurements are carried out as follows:

200 ng of FITC, dissolved in 20 ul of distilled water, are first pipetted into a test tube. The sample is then placed in the darkened measuring position in front of the photomultiplier (measuring instrument: BIOLUMAT LB 9500 from Messrs. Laboratorium Prof. Dr. Berthold, Wildbad, Federal Republic of Germany). 100 ul of NaOCl of the given dilution are then injected onto the FITC through the dispenser system.

The kinetics are followed by recording via a rate meter connected to a pen recorder. The rate meter has two time constants of 20 ms and 1 s, the short time automatically being switched in for rapid changes and the long time being switched in for slow changes. At the same time, the number of pulses is integrated over a period of preferably, 10 s.

Example II

In a second series of experiments, solutions with varying FITC concentrations are produced.

For this, various amounts of unbound FITC (protein free) in the range from 1.25 ng to 200 ng, in each case dissolved in 20 ul of distilled water are added, in each case 100 ul of diluted NaOCl (2.5 g chlorine per liter) are then applied, and the measurements are taken.

The results of these measurements are shown in FIG. 2 and it can be seen that perfect linearity over the entire range is obtained. The limits were determined only by measuring conditions available at the time. Towards higher concentrations problems appear as it becomes increasingly difficult to dissolve the available amount of FITC in water, while towards lower concentrations, a further factor of 10 can easily be achieved by lowering the zero effect due to the measuring instrument, for example by cooling the photomultiplier.

A further increase in sensitivity by about two orders of magnitude was surprisingly discovered when the FITC is present in protein bound form instead of being unbound.

Example III

The process according to the invention is employed to detect the HB antigen (herein abbreviated as $HB_sAg$), also known as hepatitis B antigen.

This is a solid phase assay. Human anti $HB_s$ (antibodies) are coupled to the solid phase in a known manner (solid phase: polystyrene spheres or microtiter plate). After subsequent saturation of the solid phase with calf serum, the solid phase is ready for use.

The solid phase is then incubated with the serum sample to be examined for $HB_sAg$ (0.1 or 0.2 ml). For the fast test, the incubation period is 2 hours at 37° C. For the standard test, the incubation period is 16 hours at room temperature. Then the samples are thoroughly rinsed with a conventional phosphate buffer which may have the following composition, for example:

NaCl: 8.0 g
KCl: 0.2 g
$Na_2HPO_4 \cdot 12H_2O$: 2.89 g
$KH_2PO_4$: 0.2 g
aqua bidest.: up to 1000 ml Any $HB_s$ antigen present in the serum sample is now bound to the solid phase.

Then the tracer is added. FITC marked human anti $HB_s$, which had been obtained affinity chromatographically, is used as the tracer. The solid phase with the tracer is incubated for four hours at room temperature. Thereafter, the sample is again rinsed thoroughly with phosphate buffer. The tracer now has bound the $HB_sAg$ adhering to the solid phase.

The serum sample to be examined is used undiluted, as well as in different concentrations, diluted with normal human serum. However, phosphate buffer can also be used as the diluent, if necessary with the addition of $NaN_3$ (0.1% solution) which has a bactericide effect and inhibits the growth of bacteria in the serum samples.

After the addition of aqueous NaOCl solution (25 g Cl/liter) to the individual solid phases with tracer bound thereto, the samples are measured and the pulse rate is determined in dependence on the serum concentration. The results obtained thereby are shown in FIG. 3 where the abscissa shows the concentrations of $HB_s$ antigens in the serum in ng/ml and the ordinate shows the pulse rate in $10^3$ units.

The detection limit for the serum concentration for $HB_sAg$ is 0.1 ng/ml. The curve in FIG. 3 can also be used as the calibration curve for the determination of unknown $HB_sAg$ concentrations in serum samples.

Decisive advantages of the process according to the present invention are:

1. Only a single reagent (instead of two in other cases) need be added in order to trigger off the chemiluminescence reaction; the measuring instrument can thus be simplified because only one, not two, automatic injectors is required.
2. The zero value is now only determined by the instrument itself. In contrast, if two reagents are required, in addition to the FITC, these usually produce a considerable luminescence, as an interfering factor, ever in the absence of FITC.
3. Only with this system could perfect linearity be established between the indication and the FITC amount over an initial concentration range of $10^0$ to $2 \times 10^2$ which corresponds to a factor of 200. (FIG. 2)
4. For protein bound FITC, a broad concentration range can be covered without problems, the curve in FIG. 3 being noticeably flatter for very small concentrations than in the concentration range from 10 to 1000 ng/ml.

It will be understood that the above description of the present invention is susceptible to various modifications, changes and adaptations, and the same are intended to be comprehended within the meaning and range of equivalents of the appended claims.

What is claimed is:

1. Process for carrying out an analytical determination of the presence of a substance by means of chemiluminescence, comprising employing fluorescein isothiocyanate (FITC) as a labelling agent, triggering a chemiluminescence reaction by adding an aqueous solution of sodium hypochlorite, and measuring the emission of light.

2. Process according to claim 1, wherein the determination is carried out in an aqueous medium, without the addition of other oxidixing agents and/or reducing agents for the chemiluminescence reaction.

3. Process according to claim 1 or claim 2, wherein the light emitted is measured by means of an instrument in which the quanta of light are detected by a photomultiplier and the individual pulses triggered off by the photons are counted.

4. Process as defined in claims 1 or 2, wherein the sodium hypochlorite solution contains 2 to 100 g Cl/liter.

5. Process as defined in claim 4, wherein a sodium hypochlorite solution containing 2.5 g Cl/liter is used for the determination of protein free FITC.

6. Process as defined in claim 4, wherein a sodium hypochlorite solution containing 25 g Cl/liter is used for the determination of protein bound FITC.

7. Process as defined in claims 1 or 2, wherein distilled water, phosphate buffer or a mixture of phosphate buffer and $NaN_3$ solution is used as a diluent for the substance.

8. Process according to claims 1 or 2, wherein the analytical determination is an immunoassay.

9. Process for carrying out an analytical determination of the presence of a substance by means of chemiluminescence, comprising:
    (a) bringing together the substance, a binding agent for the substance, and fluorescein isothiocyanate (FITC) as a labelling agent to form a coupled product,
    (b) adding an aqueous solution of sodium hypochlorite to the coupled product to trigger a chemiluminescence reaction, and
    (c) measuring the emission of light from the chemiluminescence reaction.

10. Process as defined in claim 9, wherein the substance is an antigen, the binding agent is an antibody specific for the substance and attached to a solid matrix, the substance is brought into contact with the antibody on the matrix to fix the substance, and the FITC is then coupled to the fixed substance.

11. Process as defined in claim 9, wherein the substance is an antigen which is fixed onto a solid substrate, the binding agent is an antibody, the antibody is coupled with the FITC, and the coupled antibody is contacted with the antigen.

12. Process as defined in claim 9 wherein the substance is an antigen and the binding agent is an antibody, a solid substrate with a deposit of antibody is brought into contact with a sample containing the antigen, the amount of antibody being greater than that required for bonding all the antigenic material in the sample, the substrate is then brought into contact with a solution containing antibodies modified by the FITC, so that the antigens on the substrate become attached to these labelled antibodies to form the coupled product, and the substrate is then freed from excess labelled antibody.

13. Process as defined in claim 9, wherein the substance to be determined is an antigen, antigens which are identical to the substance to be determined are bonded to a solid substrate which forms a chemical bond with an antigen such that an antibody-specific bonding point remains free, the solid substrate is then immersed in a solution containing an unknown amount of the antigen to be determined, and antibody specific to the antigen and modified by the FITC is subsequently added to form the coupled product.

14. A process for the analytical determination of an antigen or an antibody in a sample wherein immunochemical reagents are introduced into the protocol and wherein one of said immunochemical reagents is labeled with fluorescein isothiocyanate the improvement comprising:
    contacting the fluorescein isothiocyanate-containing immunochemical product formed during the protocol with an aqueous solution consisting essentially of water and sodium hypochlorite, said contacting producing a chemiluminescent reaction between the fluorescein isothiocyanate label and the sodium hypochlorite and measuring the emitted light of the chemiluminescent reaction.

* * * * *